(12) United States Patent
Amtmann et al.

(10) Patent No.: US 6,447,660 B2
(45) Date of Patent: *Sep. 10, 2002

(54) CIRCUIT CONFIGURATION FOR CONTROLLING A PUMP CURRENT OF AN EXHAUST PROBE IN A MOTOR VEHICLE

(75) Inventors: Markus Amtmann, Regensburg; Stephan Bolz, Pfatter; Jürgen Rössler, Münnerstadt, all of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/781,613

(22) Filed: Feb. 12, 2001

Related U.S. Application Data

(63) Continuation of application No. PCT/DE99/02488, filed on Aug. 10, 1999.

(30) Foreign Application Priority Data

Aug. 10, 1998 (DE) .......................... 198 36 128

(51) Int. Cl.$^7$ ............................ G01N 27/407
(52) U.S. Cl. .................. 204/425; 204/426; 204/427; 204/406; 205/781; 205/784.5
(58) Field of Search ................ 204/421–429, 204/406

(56) References Cited

U.S. PATENT DOCUMENTS 5,675,069 A   10/1997   Schleupen et al.
5,935,400 A * 8/1999   Takami et al.
6,059,947 A * 5/2000   Kato et al.

FOREIGN PATENT DOCUMENTS

DE    198 32 128 A1    2/2000
EP    0 507 149 a1     10/1992

OTHER PUBLICATIONS

"Performance of Thick Film NO$_x$ Sensor on Diesel and Gasoline Engines" (Kato et al.), dated 1997, Xp–000866024, pp.1246–1253

* cited by examiner

Primary Examiner—T. Tung
(74) Attorney, Agent, or Firm—Laurence A. Greenberg; Werner H. Stemer; Ralph E. Locher

(57) ABSTRACT

A circuit configuration for controlling a pump current includes a microcontroller, an analog circuit and a read-only memory. A pulse-width modulated signal, which is output by the micro-controller, is converted, by using the analog circuit, into the pump current for a pump cell of an exhaust probe which operates according to the principle of the galvanic oxygen concentration cell with a solid electrolyte. A pump current actual value is determined from a voltage drop across a measuring resistor, and a pump current setpoint value is determined from a voltage difference between an actual value of a Nernst voltage in the corresponding measuring cell and a predefined setpoint value. An exhaust probe configuration is also provided.

20 Claims, 3 Drawing Sheets

CIRCUIT CONFIGURATION FOR CONTROLLING A PUMP CURRENT OF AN EXHAUST PROBE IN A MOTOR VEHICLE

CROSS-REFERENCE TO RELATED APPLICATION

This application is a continuation of copending International Application No. PCT/DE99/02488, filed Aug. 10, 1999, which designated the United States.

BACKGROUND OF THE INVENTION

Field of the Invention

The invention relates to a circuit configuration for controlling a pump current of an exhaust probe in a motor vehicle.

As environmental awareness is increasing and resulting exhaust gas regulations are becoming increasingly strict, the need to reduce pollutants in exhaust gases of internal combustion engines in motor vehicles is becoming increasingly important. Compliance with currently valid emission limits for pollutants such as carbon monoxide (CO), nitrogen oxides ($NO_x$) and hydrocarbons (HC) requires, on the one hand, a specific engine control and, on the other hand, a catalytic post-treatment of the exhaust gases. For both measures it is necessary to obtain measurement values with exhaust gas probes—for example lambda probes or $NO_x$ probes. In the following, the term probe designates a unit including a sensor, a sensor line and a sensor plug.

It is known to use thick film sensors to measure the concentration of pollutants in the exhaust gas of an internal combustion engine. Such a sensor is described, using the example of a $NO_x$ sensor, by N. Kato et al. in the publication "Performance of Thick Film $NO_x$ Sensor on Diesel and Gasoline Engines", Society of Automotive Engineers, Publication 970858, 1997. This $NO_x$ sensor has two measuring cells and three oxygen pump cells and implements the following measuring concept: in a first measuring cell to which the gas to be measured is fed via a diffusion barrier, a first oxygen concentration is set through the use of a first oxygen ion pump current, wherein no $NO_x$ is decomposed. In a second measuring cell, which is connected to the first measuring cell via a diffusion barrier, the oxygen content is reduced further through the use of a second oxygen ion pump current and $NO_x$ is decomposed at a measuring electrode. The oxygen which is generated in this way is used as a measure of the $NO_x$ concentration. The entire $NO_x$ sensor is heated to an increased temperature, for example 700° C., through the use of an electric heating element.

In order to operate such a sensor it is necessary to regulate the respective pump current for the oxygen pump cells precisely.

SUMMARY OF THE INVENTION

It is accordingly an object of the invention to provide a circuit configuration which can control the pump currents for the oxygen pump cells in a precise manner.

With the foregoing and other objects in view there is provided, in accordance with the invention, in combination with an exhaust probe having a solid electrolyte, a pump cell and a measuring cell, and operating according to a principle of a galvanic oxygen concentration cell, a circuit configuration for controlling a pump current for the pump cell, including:

a microcontroller for determining a pump current actual value at the pump cell to be controlled, the microcontroller determining an actual value of a Nernst voltage at the measuring cell, and the microcontroller generating a pulse-width-modulated signal;

an analog circuit connected to the microcontroller, the analog circuit converting the pulse-width-modulated signal into the pump current for the pump cell; and a read-only memory operatively connected to the microcontroller, the read-only memory providing a setpoint value of the Nernst voltage.

According to a preferred embodiment of the invention, a microcontroller in conjunction with an analog circuit is used to control the required pump currents. In order to determine the respective pump current, the voltage drop across a measuring resistor which is preferably connected directly upstream of the corresponding pump cell is measured using A/D converters in the microcontroller. In this way, the measuring error of the entire circuit configuration is reduced to the tolerance of the measuring resistors and the errors of the A/D conversions caused by leakage currents and quantization errors.

According to another feature of the invention, the read-only memory is a programmable read-only memory.

According to yet another feature of the invention, the read-only memory is integrated into the microcontroller.

According to a further feature of the invention, a measuring resistor is connected upstream of the pump cell to be controlled, and the microcontroller determines the pump current actual value from a voltage drop across the measuring resistor.

According to another feature of the invention, the microcontroller includes a first difference former, a second difference former, a first controller, a second controller, and a pulse-width modulation unit. The first difference former forms a voltage difference from the actual value of the Nernst voltage and the setpoint value of the Nernst voltage. The first controller forms a pump current setpoint value from the voltage difference. The second difference former forms a pump current difference value from the pump current actual value and the pump current setpoint value. The pulse-width modulation unit generates the pulse-width-modulated signal, and the second controller controls the pulse-width modulation unit based on the pump current difference value.

According to another feature of the invention, the microcontroller includes an first A/D converter and a third difference former. A measuring resistor is connected upstream of the pump cell to be controlled. The first A/D converter reads voltage potentials upstream and downstream of the measuring resistor, and the third difference former determines the pump current actual value from the voltage potentials read by the A/D converter.

According to a further feature of the invention, the microcontroller includes a second A/D converter and a fourth difference former. The second A/D converter reads a Nernst potential and a reference potential at the measuring cell, and the fourth difference former determines the actual value of the Nernst voltage from the Nernst potential and the reference potential.

According to another feature of the invention, the analog circuit includes a filter circuit and an impedance converter. The filter circuit converts the pulse-width-modulated signal into a DC voltage signal, and the impedance converter adapts an output impedance of the microcontroller as a function of a required current strength.

According to yet another feature of the invention, a sensor plug housing for the exhaust probe is provided, and the microcontroller, the analog circuit, and the read-only memory are integrated in the sensor plug housing.

With the objects of the invention in view there is also provided, an exhaust probe configuration, including:

an exhaust probe including a solid electrolyte, a pump cell, and a measuring cell, the exhaust probe operating according to a principle of a galvanic oxygen concentration cell;

a circuit configuration connected to the exhaust probe for controlling a pump current for the pump cell;

the circuit configuration including a microcontroller, an analog circuit, and a read-only memory;

the microcontroller determining a pump current actual value at the pump cell to be controlled, the microcontroller determining an actual value of a Nernst voltage at the measuring cell, and the microcontroller generating a pulse-width-modulated signal;

the analog circuit being connected to the microcontroller, the analog circuit converting the pulse-width-modulated signal into the pump current for the pump cell; and the read-only memory providing a setpoint value of the Nernst voltage.

Other features which are considered as characteristic for the invention are set forth in the appended claims.

Although the invention is illustrated and described herein as embodied in a circuit configuration for controlling a pump current of an exhaust probe in a motor vehicle, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
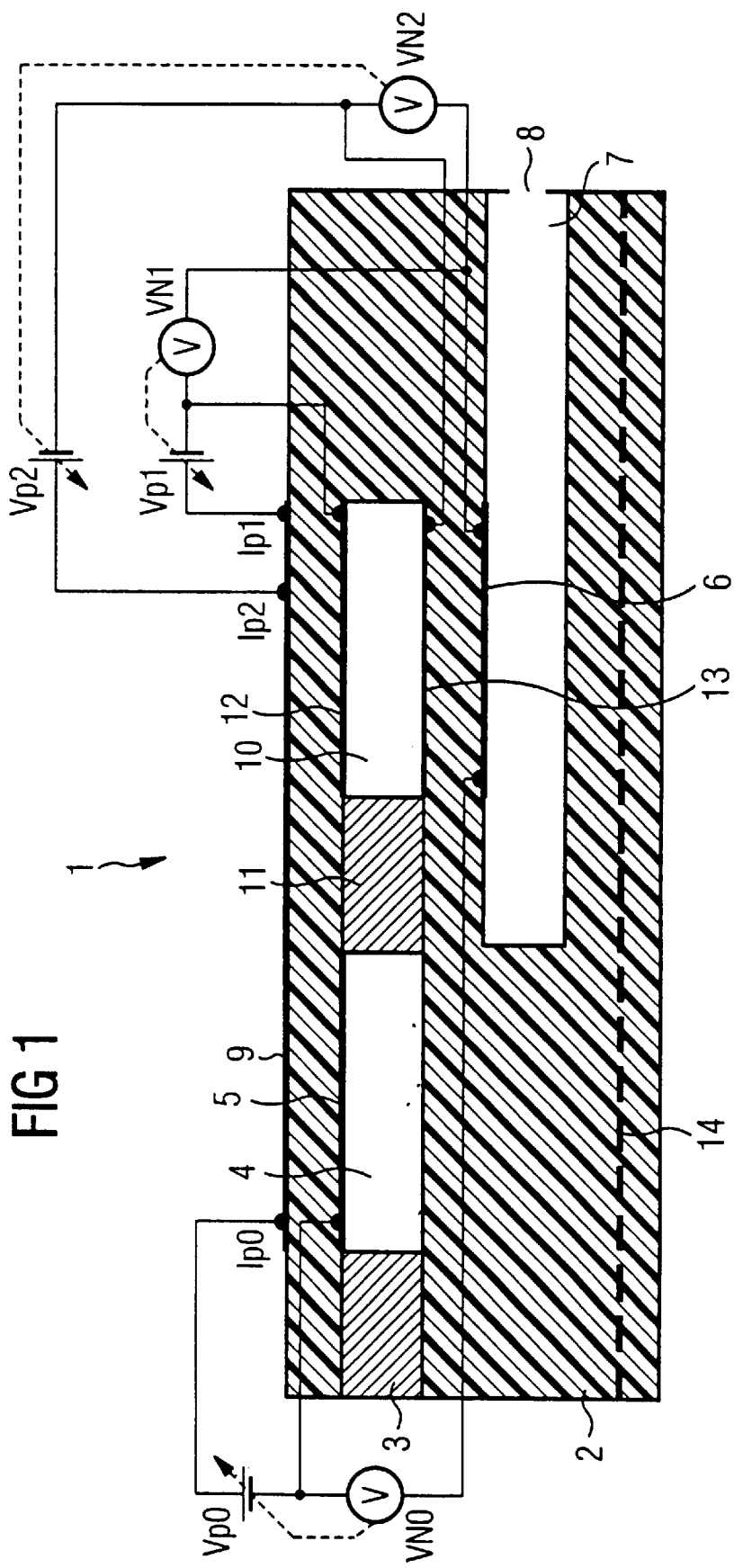
FIG. 1 is a diagrammatic sectional view of a $NO_x$ sensor.

Referring now to the figures of the drawings in detail and first, particularly, to FIG. 1 thereof, there is shown a schematic sectional illustration of a $NO_x$ sensor 1. The $NO_x$ sensor 1 which is composed of a solid (solid-state) electrolyte 2, in this case zirconium dioxide, receives the exhaust gas to be measured via a first diffusion barrier 3. The exhaust gas diffuses through the diffusion barrier 3 into a first measuring cell 4. The oxygen content in this measuring cell is measured from a first Nernst voltage VN0 between a first pump electrode 5 and a reference electrode 6 which is exposed to ambient air. The reference electrode 6 here is provided in an air duct 7 into which ambient air passes via an opening 8. Both electrodes 5, 6 are conventional platinum electrodes.

According to a general method, the measured value of the first Nernst voltage VN0 is used to set a first control voltage or regulating voltage Vp0. The control voltage Vp0 drives a first oxygen ion pump current Ip0 through the solid electrolyte 2 of the $NO_x$ sensor 1 between the first pump electrode 5 and an external electrode 9 —the pump electrode 5 and the external electrode 9 form a first pump cell. Here, the control voltage Vp0 is set by a controller in such a way that a predefined oxygen concentration is present in the first measuring cell 4.

The first measuring cell 4 is connected to a second measuring cell 10 via a second diffusion barrier 11. The gas present in the measuring cell 4 diffuses into the second measuring cell 10 through this diffusion barrier 11. The second oxygen concentration in the second measuring cell 10 is measured through the use of a second Nernst voltage VN1 between a second pump electrode 12, which is also a platinum electrode, and the reference electrode 6 and is used by a controller to set a second control voltage Vp1 which drives a second oxygen ion pump current Ip1. The second oxygen ion pump current Ip1 from the second measuring cell 10 flows from the second pump electrode 12 through the solid electrolyte 2 to the external electrode 9 (second pump cell). The second oxygen ion pump current Ip1 is used to set a predefined oxygen concentration in the second measuring cell 10.

The $NO_x$ concentration which is not affected by the previous processes in the measuring cells 4 and 10 is now determined at a measuring electrode 13 which is configured to be catalytically active. For this purpose, a third oxygen concentration is measured through the use of a third Nernst voltage VN2 between the measuring electrode 13 and the reference electrode 6 and is used by a controller to set a third control voltage Vp2. By applying this control voltage Vp2 between the measuring electrode 13 and the external electrode 9 (third pump cell), the $NO_x$ is decomposed and the released oxygen is pumped through the solid electrolyte 2 in a third oxygen ion pump current Ip2 to the external electrode 9. When the residual oxygen content in the measuring cell 10 is sufficiently low, the third oxygen ion pump current Ip2 is conducted only by oxygen ions which originate from the decomposition of $NO_x$. The third oxygen ion pump current Ip2 is thus a measure of the $NO_x$ concentration in the measuring cell 10 and thus in the exhaust gas to be measured. Because such $NO_x$ sensors are highly dependent on temperature, a heating element 14 ensures that the probe temperature is always kept in a predefined temperature range in order to maintain the necessary measuring accuracy.

Figure 2:
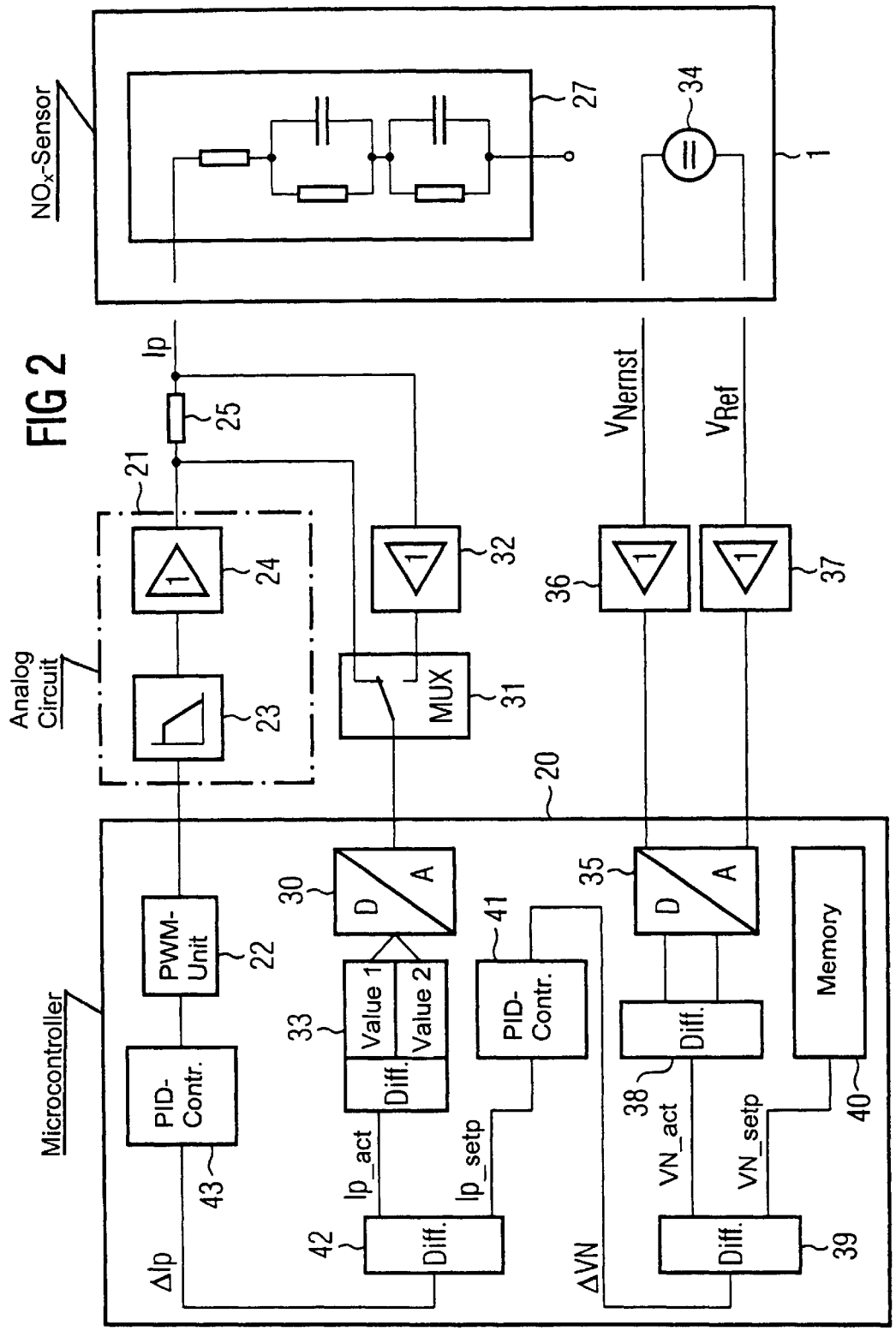
FIG. 2 is a block circuit diagram of the circuit configuration according to the invention for controlling a pump current.

A microcontroller 20 in conjunction with an analog circuit 21 is used to control the pump currents. The circuit configuration of an individual pump current control circuit is illustrated in detail in FIG. 2. The control circuit of the entire $NO_x$ sensor has such a circuit configuration for each pump cell to be controlled. Here, the necessary digital circuit components can be implemented within a single microcontroller 20. A PWM (Pulse Width Modulation) unit 22 in the microcontroller 20 generates a pulse-width-modulated signal which is converted into a DC voltage using an analog filter circuit 23. Depending on the current strength required, this voltage is either fed directly or via an impedance converter 24 to a measuring resistor 25 which is connected in series with the pump cell 27 of the $NO_x$ sensor 1, wherein the pump cell 27 is to be controlled. The pump cell is illustrated in FIG. 2 in the form of an equivalent circuit of the associated impedance.

The voltage potentials upstream (value 1) and downstream (value 2) of the measuring resistor 25 are alternately read in through the use of a multiplexer 31 using a first A/D converter 30 in the microcontroller 20. Because the input of the $NO_x$ sensor 1 usually has a very high impedance, an impedance converter 32, for example a buffer amplifier, can be connected into the measuring line which is used for measuring the potential value downstream of the measuring resistor 25. A first discrete difference former 33 determines the pump current actual value Ip_act from a respective potential value upstream and a respective potential value downstream of the measuring resistor 25.

The Nernst voltages required to control the pump currents are also calculated in the microcontroller 20. To do this, both the Nernst potential $V_{Nernst}$ and the reference potential $V_{ref}$ of the appropriate measuring cell 34 of the $NO_x$ sensor 1 are read in by a second A/D converter 35 in the microcontroller 20. The measuring cell 34 corresponds here either to the first measuring cell 4 or to the second measuring cell 10 in FIG. 1 depending on the pump cell 27 to be controlled, and the measuring cell 34 is illustrated schematically as DC voltage source. Here too, impedance converters 36 and 37, for example in the form of buffer amplifiers, can be used to adapt the high output impedance of the $NO_x$ sensor 1 to the impedance of the inputs of the microcontroller 20. A second difference former 38 in the microcontroller 20 determines the actual value of the Nernst voltage VN_act from the read-in potential values. In a third difference former 39, the actual value of the Nernst voltage VN_act is then compared with a setpoint value VN_setp. This setpoint value is read out of a read-only memory 40, which is preferably integrated into the microcontroller 20. If a programmable read-only memory, for example an EPROM (Erasable Programmable Read only Memory), is used here, it is possible to compensate asymmetries which may occur, or to recalibrate during the service life of the sensor.

A pump current setpoint value Ip_setp is formed from the voltage difference ΔVN between the actual value VN_act and the setpoint value VN_setp of the Nernst voltage through the use of a first controller 41, for example a PID controller, within the microcontroller 20. A fourth difference former 42 forms a pump current difference ΔIp from the actual value and the setpoint value of the pump current, the pump current difference ΔIp being fed to a second controller 43, for example a PID controller, which is provided within the microcontroller 20 and controls the PWM unit 22.

Figure 3:
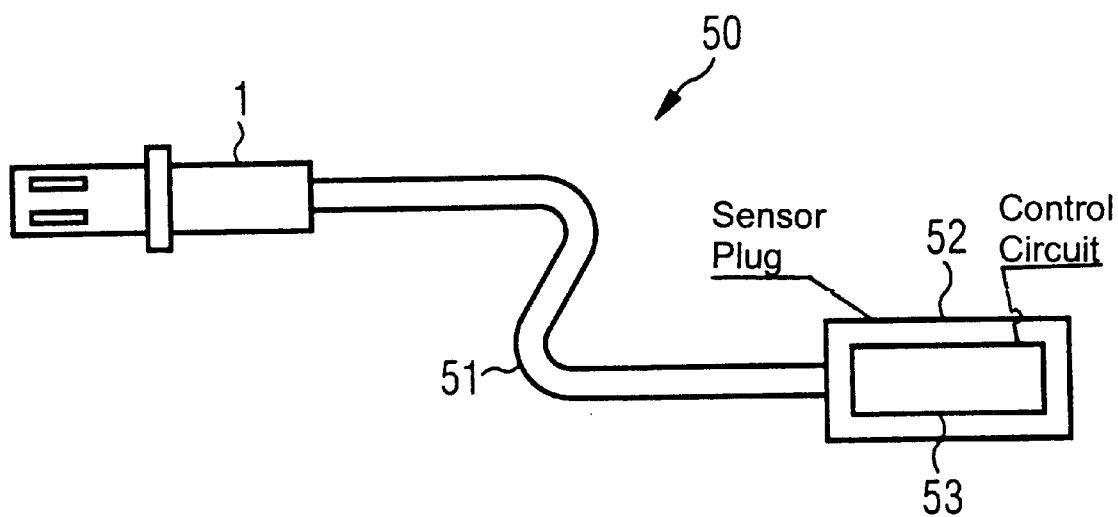
FIG. 3 is a diagrammatic plan view of a $NO_x$ probe.

As illustrated in FIG. 3, a $NO_x$ probe 50 has, in addition to the $NO_x$ sensor 1, a sensor line 51 and a sensor plug 52. Because the signal currents of the $NO_x$ sensor 1 are usually only in the nA range, the length of the connecting lines between the sensor 1 and the control electronics 53 influences the precision of the signal transmission considerably. Integrating the control circuit 53 into the housing of the sensor plug 52 ensures that the signals are transmitted with the necessary precision despite the occurrence of leakage currents.

As a result of the use of a microcontroller with integrated A/D converters, it is possible to read various voltage potentials within the circuit configuration and further process them as desired through the use of difference formation. In this way, it is possible to dispense with an additional analog formation of differences with the corresponding tolerance errors. In comparison with a purely analog circuit configuration, the combination of a microcontroller with an analog circuit thus permits the overall error of the circuit to be reduced to the tolerance of the measuring resistor and the errors of the A/D conversion, that is to say quantization errors and leakage currents which occur. A high level of reliability of the system is ensured by the low degree of complexity of the circuit and the robust circuit configuration.

The invention has been described by way of example for a $NO_x$ sensor, but it is to be noted that corresponding circuit configurations are also suitable for other exhaust probes which operate according to the principle of the galvanic oxygen concentration cell with a solid electrolyte, for example linear oxygen probes.

We claim:

1. In combination with an exhaust probe having a solid electrolyte, a pump cell and a measuring cell, and operating according to a principle of a galvanic oxygen concentration cell, a circuit configuration for controlling a pump current for the pump cell, comprising:

a microcontroller for determining a pump current actual value at the pump cell to be controlled, said microcontroller determining an actual value of a Nernst voltage at the measuring cell, and said microcontroller generating a pulse-width-modulated signal;

an analog circuit connected to said microcontroller, said analog circuit converting the pulse-width-modulated signal into the pump current for the pump cell; and a read-only memory operatively connected to said microcontroller, said read-only memory providing a setpoint value of the Nernst voltage.

2. The circuit configuration according to claim 1, wherein said read-only memory is a programmable read-only memory.

3. The circuit configuration according to claim 1, wherein said read-only memory is integrated into said microcontroller.

4. The circuit configuration according to claim 1, including:

a measuring resistor connected upstream of the pump cell to be controlled; and said microcontroller determining the pump current actual value from a voltage drop across said measuring resistor.

5. The circuit configuration according to claim 1, wherein:

said microcontroller includes a first difference former, a second difference former, a first controller, a second controller, and a pulse-width modulation unit;

said first difference former forming a voltage difference from the actual value of the Nernst voltage and the setpoint value of the Nernst voltage;

said first controller forming a pump current setpoint value from the voltage difference;

said second difference former forming a pump current difference value from the pump current actual value and the pump current setpoint value;

said pulse-width modulation unit generating the pulse-width-modulated signal; and said second controller controlling said pulse-width-modulation unit based on the pump current difference value.

6. The circuit configuration according to claim 5, wherein:

said microcontroller includes an A/D converter and a third difference former;

a measuring resistor is connected upstream of the pump cell to be controlled;

said A/D converter reads voltage potentials upstream and downstream of said measuring resistor; and said third difference former determines the pump current actual value from the voltage potentials read by said A/D converter.

7. The circuit configuration according to claim 6, wherein:

said A/D converter is a first A/D converter;

said microcontroller includes a second A/D converter and a fourth difference former;

said second A/D converter reads a Nernst potential and a reference potential at the measuring cell; and said fourth difference former determines the actual value of the Nernst voltage from the Nernst potential and the reference potential.

8. The circuit configuration according to claim 5, wherein:

said microcontroller includes an A/D converter and a third difference former;

said A/D converter reads a Nernst potential and a reference potential at the measuring cell; and said third difference former determines the actual value of the Nernst voltage from the Nernst potential and the reference potential.

9. The circuit configuration according to claim 1, wherein:

said microcontroller has an output impedance;

said analog circuit includes a filter circuit and an impedance converter;

said filter circuit converts the pulse-width-modulated signal into a DC voltage signal; and said impedance converter adapts the output impedance of said microcontroller as a function of a required current strength.

10. The circuit configuration according to claim 1, including:

a sensor plug housing for the exhaust probe; and said microcontroller, said analog circuit, and said read-only memory being integrated in said sensor plug housing.

11. An exhaust probe configuration, comprising:

an exhaust probe including a solid electrolyte, a pump cell, and a measuring cell, said exhaust probe operating according to a principle of a galvanic oxygen concentration cell;

a circuit configuration connected to said exhaust probe for controlling a pump current for said pump cell;

said circuit configuration including a microcontroller, an analog circuit, and a read-only memory;

said microcontroller determining a pump current actual value at said pump cell to be controlled, said microcontroller determining an actual value of a Nernst voltage at the measuring cell, and said microcontroller generating a pulse-width-modulated signal;

said analog circuit being connected to said microcontroller, said analog circuit converting the pulse-width-modulated signal into the pump current for said pump cell; and said read-only memory providing a setpoint value of the Nernst voltage.

12. The exhaust probe configuration according to claim 11, wherein said read-only memory is a programmable read-only memory.

13. The exhaust probe configuration according to claim 11, wherein said read-only memory i s integrated into said microcontroller.

14. The exhaust probe configuration according to claim 11, including:

a measuring resistor connected upstream of said pump cell to be controlled; and said microcontroller determining the pump current actual value from a voltage drop across said measuring resistor.

15. The exhaust probe configuration according to claim 11, wherein:

said microcontroller includes a first difference former, a second difference former, a first controller, a second controller, and a pulse-width modulation unit;

said first difference former forming a voltage difference from the actual value of the Nernst voltage and the setpoint value of the Nernst voltage;

said first controller forming a pump current setpoint value from the voltage difference;

said second difference former forming a pump current difference value from the pump current actual value and the pump current setpoint value;

said pulse-width modulation unit generating the pulse-width-modulated signal; and said second controller controlling said pulse-width-modulation unit based on the pump current difference value.

16. The exhaust probe configuration according to claim 15, wherein:

said microcontroller includes an A/D converter and a third difference former;

a measuring resistor is connected upstream of the pump cell to be controlled;

said A/D converter reads voltage potentials upstream and downstream of said measuring resistor; and said third difference former determines the pump current actual value from the voltage potentials read by said A/D converter.

17. The exhaust probe configuration according to claim 16, wherein:

said A/D converter is a first A/D converter;

said microcontroller includes a second A/D converter and a fourth difference former;

said second A/D converter reads a Nernst potential and a reference potential at the measuring cell; and said fourth difference former determines the actual value of the Nernst voltage from the Nernst potential and the reference potential.

18. The exhaust probe configuration according to claim 15, wherein:

said microcontroller includes an A/D converter and a third difference former;

said A/D converter reads a Nernst potential and a reference potential at the measuring cell; and said third difference former determines the actual value of the Nernst voltage from the Nernst potential and the reference potential.

19. The exhaust probe configuration according to claim 11, wherein:

said microcontroller has an output impedance;

said analog circuit includes a filter circuit and an impedance converter;

said filter circuit converts the pulse-width-modulated signal into a DC voltage signal; and said impedance converter adapts the output impedance of said microcontroller as a function of a required current strength.

20. The exhaust probe configuration according to claim 11, including:

a sensor plug housing; and said microcontroller, said analog circuit, and said read-only memory being integrated in said sensor plug housing.

* * * * *